United States Patent [19]

Carpenter et al.

[11] Patent Number: 4,562,844
[45] Date of Patent: Jan. 7, 1986

[54] MULTIPURPOSE SYRINGE

[75] Inventors: Tristram Carpenter, Norwood; Michael Gorker, Sharon, both of Mass.

[73] Assignee: Jett Labs, Inc., Norwood, Mass.

[21] Appl. No.: 675,140

[22] Filed: Nov. 27, 1984

[51] Int. Cl.⁴ ............................................. A61B 5/00
[52] U.S. Cl. .................................... 128/675; 604/220; 604/228
[58] Field of Search ............... 128/760, 765; 604/218, 604/220, 222, 228, 110, 111

[56] References Cited

U.S. PATENT DOCUMENTS

| | | | |
|---|---|---|---|
| 2,688,325 | 9/1954 | Lockhart | 604/220 |
| 3,013,557 | 12/1961 | Pallotta | 128/218 |
| 3,459,183 | 8/1969 | Ring et al. | 604/165 X |
| 3,577,980 | 5/1971 | Cohen | 128/2 |
| 3,937,211 | 2/1976 | Merten | 128/2 F |
| 4,036,232 | 7/1977 | Genese | 128/765 X |
| 4,459,997 | 7/1984 | Sarstedt | 128/765 X |

OTHER PUBLICATIONS

"VACUTAINER Brand Evacuated Blood Collection Tube", Becton Dickinson VACUTAINER Systems, Rutherford, New Jersey 07070 5/80-09-P10259 (DE).

Primary Examiner—Dalton L. Truluck
Attorney, Agent, or Firm—Hamilton, Brook, Smith & Reynolds

[57] ABSTRACT

A multipurpose syringe for obtaining a blood sample and for storing and shipping it having a barrel (10), a plunger (32), and a rod (36), and means (40) (42) (44) for locking the plunger in retracted position.

19 Claims, 14 Drawing Figures

MULTIPURPOSE SYRINGE

FIELD OF THE INVENTION

This invention relates to syringes in general and more specifically to a multipurpose syringe for obtaining a blood sample and for storing and shipping it.

BACKGROUND OF THE INVENTION

Problems can arise after blood has been drawn by a syringe in transferring it by mail or other delivery means to a location for testing or centrifugation. Historically, blood has been removed from the syringe and transferred to a shipping container which is then sealed and shipped to a laboratory for further processing. Transferring a blood specimen from a syringe to another container increases the possibility of contamination which can influence the analysis, if one is to be made, or the blood can infect one who may come in contact with it.

To counteract these problems, multipurpose syringes have been developed which not only serve to draw blood, but the syringe itself becomes the storing and shipping container. One such syringe is sold under the trademark VACUTAINER by Becton Dickinson & Company of Rutherford, N.J. The VACUTAINER syringe includes an evacuated glass tube containing a pre-measured vacuum to provide a controlled, pre-specified draw. The glass tube is closed by a resealable plug in its forward end, the opposite end being permanently closed. The tube slides into the open end of a cylindrical holder which, at the other end, has a hollow needle or spike projecting inwardly and a venipuncture needle projecting outwardly from the plug. The venipuncture needle is inserted in a vein and the fixed vacuum tube slid into the holder until the rearwardly projecting spike pierces the plug and allows the vacuum within the glass tube to draw a measured quantity of blood from the vein. The glass tube is subsequently withdrawn from the holder whereupon the plug self-seals and the entire plugged tube may be shipped to a laboratory for further processing.

While this type of syringe is in common use, it is somewhat restricted because it will only draw a pre-specified amount of blood due to the fixed vacuum in the sealed glass tube.

Where it is desired to withdraw a pre-selected amount of blood, or to control the amount of vacuum that a vein is subjected to, plunger-operated syringes are employed. An example is found in U.S. Pat. No. 3,013,557 to Pallotta. The Pallotta syringe employs a barrel which is open at both ends, the forward end of which has means for mounting a venipuncture needle and the rearward end of it which is tapered into a conical configuration. A plunger is slidable within the barrel being attached to a plunger rod which is drawn away from the needle to draw a blood specimen. The plunger is tapered and upon entering the tapered conical portion of the barrel, becomes firmly wedged to seal the barrel. The needle is removed and the forward end of the syringe is capped. With the plunger firmly lodged in the barrel, the withdrawn plunger rod may be then broken off and the sealed barrel containing the blood specimen shipped to a laboratory for processing. While with the Pallotta syringe is capable of drawing a pre-determined quantity of blood, and controlling the amount of vacuum, once the plunger becomes lodged in the tapered portion of the barrel it cannot be removed without pressing it forward into the cylindrical portion of the barrel where the blood sample is present. Thereafter, it becomes very difficult, if not impossible, to reseal the syringe.

Subsequently, U.S. Pat. No. 3,577,980 to Cohen disclosed a multipurpose syringe having a slidable plunger which could be locked in its rearward position to create a vacuum in the syringe for the purpose of drawing blood. However, the rearward portion of the Cohen syringe was essentially closed making it impossible the remove the plunger for the purposes of removing a specimen of blood contained within the syringe cylinder.

Thereafter, U.S. Pat. No. 3,937,211 to Mertin disclosed a multipurpose syringe having a cylindrical barrel and a slidable plunger actuated by a frangible plunger rod. The rod passes through a cap which is screwed onto threads on the rearward end of the barrel. Also on the rearward end of the plunger are threads which are engagable with mating threads in a cylindrical portion of the cap. Since the cap includes both threads engagable with mating threads on the exterior of the barrel of the syringe and threads on the plunger, a problem exists in removing the specimen from the sealed barrel: unscrewing the cap from the barrel also unscrews the cap from the plunger. The plunger would then have to be removed by gripping the plunger rod. Should it then be desired to reseal the barrel, there's no way to assure that the cap would rethread itself into the plunger while simultaneously threading onto the barrel. The reason for this is that the plunger rod is frangible and is broken off after the cap is sealed.

With the above in view, it is an object of this invention to provide a multipurpose, plunger-actuated, recappable syringe for obtaining a blood sample and for storing and shipping it as well as for controlling the amount of vacuum, obviating all of the above problems.

STATEMENT OF THE INVENTION

The invention resides in a syringe including a barrel having openings at its forward and rearward ends which are in communication with the interior of the barrel. A plunger within the barrel is slidable in sealing engagement with the inner wall of the barrel between forward and retracted positions. A plunger rod is attached to the plunger and extends out of the rearward end of the barrel.

There are means to releasably lock the plunger in its retracted position including a pair of spaced flanges of a positive discernable configuration extending outwardly from the axis of the plunger rod. The flanges are located adjacent to the rearward end of the plunger. A cap is removably secured to the rearward end of the barrel and has an opening through which the plunger rod extends. The opening is larger than the flanges on the plunger rod and is of similar discernable configuration. This opening permits the flanges to pass through the cap into and out of the barrel.

There are mating interference means associated with the flanges and the opening in the cap to lock the plunger in its retracted position. The interference means are constructed to permit both flanges to pass through the opening in the cap when they are angularly aligned with each other, and to lock the flanges to the cap, when at least one flange has passed through the opening and the interference means are rotated to a position out of alignment with each other. The plunger, per se, affects the sealing and the locking means holds it in retracted position. The rod may then be broken off and discarded and the entire barrel used as a storing and shipping container.

When it is desired to withdraw a sample from the then-sealed barrel, the cap is manually removed withdrawing the plunger with it, there being no need to touch the plunger. After a sample has been withdrawn, the plunger may be reinserted and the cap replaced in locking position over the rearward end of the barrel.

The mating interference means may include at least one projection on each flange extending outwardly from the axis of the rod. At least one slot is formed in the cap extending outwardly from the opening. The slot is larger than the projections on the flanges to permit the flanges to pass through the opening in the cap when the projections are aligned with the slot and to lock the flanges to the cap, when at least one flange has passed through the opening and the projections are rotated to a position out of alignment with the slots. The flanges in this embodiment of the invention are circular. It is within the scope of the invention that the slots may be formed in the flanges and the projections formed on the cap.

In another embodiment of the invention, the discernable configuration of the opening in the cap and the flanges may be polygons of various numbers of sides but in each instance, the number of sides on the flanges are the same as the number of sides forming the opening in the cap.

A self-sealing plug is located in the forward end of the barrel and means are provided on the forward end of the barrel for mounting an inwardly projecting needle or spike to pierce the plug as well as for mounting a venipuncture needle in alignment with the plug-piercing spike.

The above and other features of the invention including various novel details of construction and combinations of parts will now be more particularly described with reference to the accompanying drawings and pointed out in the claims. It will be understood that the particular multipurpose syringe embodying the invention is shown by way of illustration only and not as a limitation of the invention. The principles and features of this invention may be employed and varied in numerous embodiments without departing from the scope of the invention.

BEST MODE OF CARRYING OUT THE INVENTION

Figure 1:
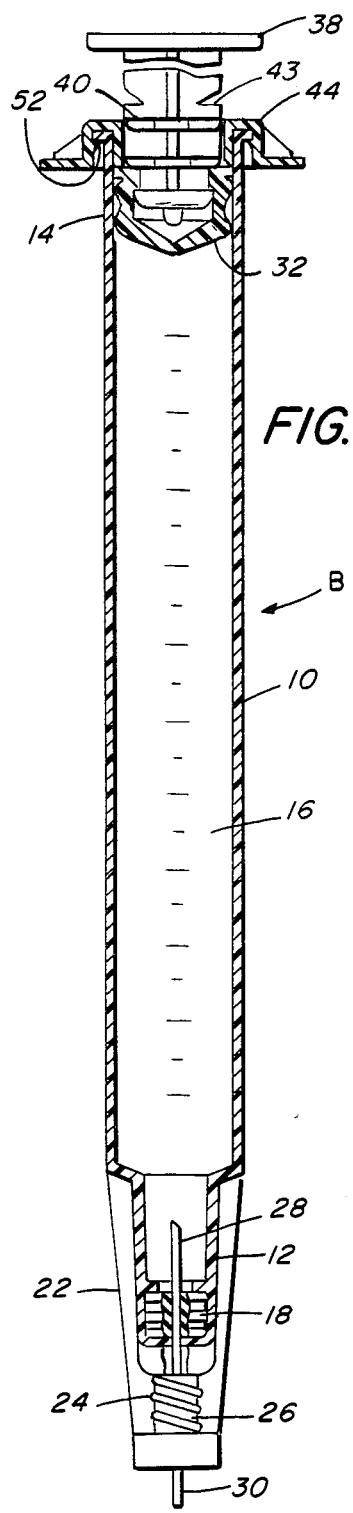
FIG. 1 is an elevational view partly in section of a multipurpose syringe embodying the features of the invention.

A multipurpose barrel syringe B is seen in FIG. 1 and includes a barrel 10 of generally cylindrical configuration, a tapered forward end portion 12 of somewhat smaller diameter than the cylindrical portion and a rearward end portion 14. The forward and rearward ends are open and communicate with the interior 16 of the barrel. A self-sealing plug 18 is fitted in the forward portion 12 of the barrel. A cap 22 fits over the tapered forward portion 12 of the barrel and includes a threaded opening 24 which receives a needle holder 26 having a rearwardly projecting hollow needle or spike 28 which when the cap 22 is placed over the tapered portion, pierces the self-sealing plug 18 and allows fluid communication between the interior 16 of the barrel and a venipuncture needle 30 of any desired gauge which may be attached to the needle holder 26 in conventional fashion. The barrel may be of glass or plastic and have volumetric indicia along its axial length to indicate the volume of blood drawn.

Figure 2:
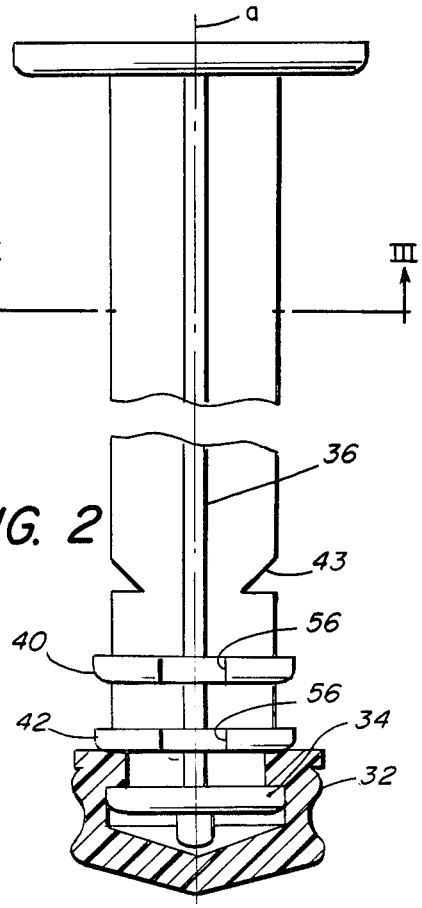
FIG. 2 is a side elevation of the plunger and plunger rod on an enlarged scale.
Figure 3:
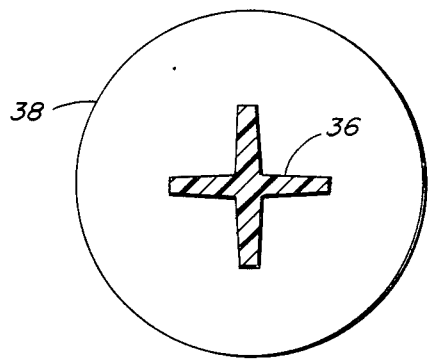
FIG. 3 is a sectional view taken on line III—III on FIG. 2.

A plunger 32 is positioned within the barrel and is slidable in sealing engagement with the inner wall of the barrel between a forward position near the tapered portion 12 and a rearward or retracted position at the end portion 14 of the barrel. Plunger 32 is flexible being made of neprine, butyl rubber, or other appropriate material. The plunger fits over a circular hub 34 on the end of a plunger rod 36 which when assembled extends lengthwise of the axis of the barrel and out of the rear open end thereof. As seen in FIG. 3 the plunger rod is cruciform in section and has a disk 38 at its rearward end which is gripped to withdraw and advance the plunger within the barrel. A pair of flanges 40 and 42 extend radially outwardly of the axis a of the plunger rod. The flanges will be described in more detail hereinafter. The plunger fits snugly up against the flange 42 as can be best seen in FIG. 2. The plunger rod 36 is notched at 44 near flange 40 to facilitate its being broken off after the plunger has been locked in its retracted position.

Figure 4:
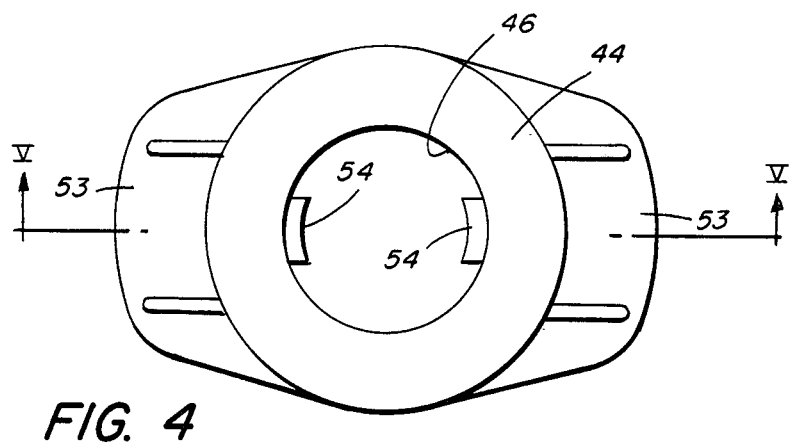
FIG. 4 is a top plan view of a locking cap.
Figure 5:
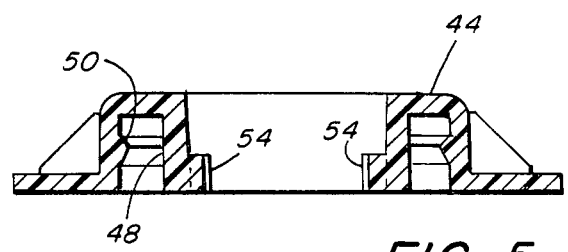
FIG. 5 is a sectional view taken on lines V—V on FIG. 4.

Referring next to FIGS. 4 and 5 there will be seen a cap 44 which is removably securable to the rearward end of the plunger barrel 10. The cap is generally circular in cross section and has an opening 46 of circular configuration which is slightly larger than the corresponding circular configuration of the flanges 40 and 42 on the plunger rod. The cap has a circular groove 48 and in it is an inwardly projecting annular rib 50 which engages beneath an outwardly extending flange 52 on the end of the barrel to facilitate its being placed on and removed from the barrel by gripping ears 53.

Figure 6:
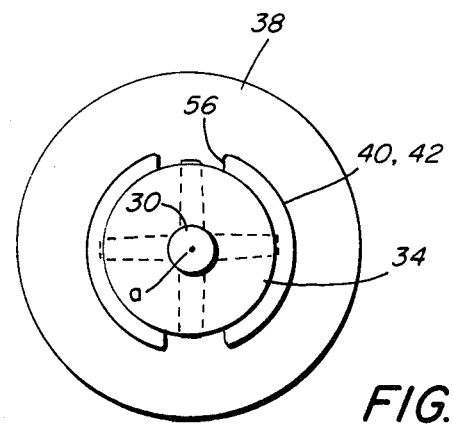
FIG. 6 is a view showing the interrelationship between the cap and the flanges on the plunger rod.

Extending inwardly from the opening 46 in the cap is at least one projection 54, two being shown diametrically opposed. For purposes of the invention, only one projection 54 is necessary. Referring next to FIG. 6 which is an end view of the plunger rod with the plunger per se removed, at least one slot 56 is formed in the flanges 40 and 42, two being shown diametrically opposed. These slots are slightly larger than the projections 54 which extend inwardly from the opening in the cap.

The syringe operates in the following manner. With the plunger either on or off the end of the plunger rod, the rod is passed through the opening in the cap with the flanges 56 in alignment with the projections 54. Since the slots are larger than the projections both flanges pass freely through the cap. It will be understood that whereas the slots 56 in the flanges 40 and 42 are in axial alignment they may be angularly offset relative to one another. With offset alignment, the slot or slots in the first flange 42 would first pass by the projections 54 on the cap. The rod would then be rotated until the slots in flange 40 are in alignment with the projections 54 permitting it to pass by the projections 54.

Once having been assembled through the cap, the plunger 32 and rod are moved into the barrel of the syringe and the cap 44 is then snapped over the flange 52 at the rearward end of the syringe. The entire syringe may then be sterilized. Next a venipuncture needle 30 is placed in the needle holder 26 in the cap 20. The cap is placed over the tapered projection 12 with the spike 28 piercing the self-sealing plug 18. This readies the syringe for usage.

The venipuncture needle is then inserted in a vein and the plunger rod drawn rearwardly. Due to the snug siding fit between the plunger 32 and the interior of the barrel, suction is created to withdraw blood. The operator is aided in delivering the amount of blood withdrawn by the volumetric indicia located on the plunger barrel. The operator also controlls the amount of vacuum created by the speed of withdrawal of the plunger, thus avoiding collapsing a vein.

Figure 7A:
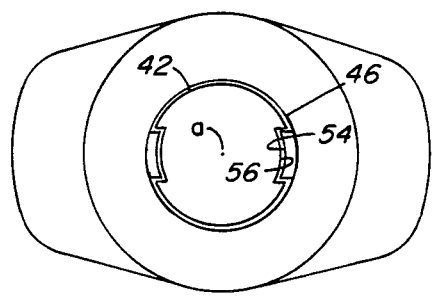
FIGS. 7-10 are schematic views showing various embodiments of the invention wherein the relationship between the plunger rod flanges and the cap are shown in both unlocked and locked relationship.
Figure 7B:
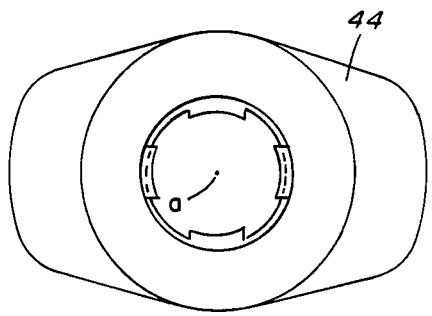

When the desired amount of blood has been drawn, the venipuncture needle is withdrawn from the vein and the plunger is moved toward the rear of the barrel ready to be locked in fully retracted position. The plunger rod is rotated to a position where the slots 56 in the flange 40 are in alignment with the projections 54 on the cap. The rod 36 is then pulled until the flanges pass through the cap. At this point, the parts occupy the position shown in FIG. 7A. After the flange 40 has passed out of the cap, the plunger rod is rotated a quarter turn whereby the projection or projections 54 lock between the flange 40 and the flange 42. At this point, the parts will occupy the position shown in FIG. 7B. This will give adequate holding power to permit the rod to be broken at the notch 43. The barrel has thus become a vial for holding a sample of blood. If desired the second flange 42 may be withdrawn from the barrel by aligning these slots and projections as above described. Again the rod would be rotated to the FIG. 7B position whereupon the projections 54 will lock between the flange 42 and the flexible plunger 34. Again, the rod may be broken and discarded. If the slots on flanges 40 and 42 are not formed in alignment with each other, the procedure is the same, but the degree of rotation of the plunger rod is varied to effect alignment. In either instance the plunger is the member which effects the seal with the barrel and the cap and flange produce the interlock.

When so assembled, the cap may be taken off the end of the barrel with the plunger fixed to it in order that a sample of blood may be removed from the barrel. Without touching the plunger or otherwise contaminating it, it may be replaced by pressing it into the barrel and snapping the cap again over the flange 52 on the end of the barrel.

Figure 8A:
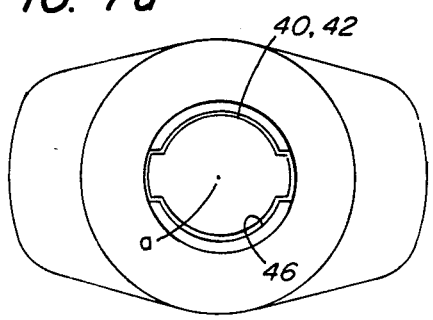
Figure 8B:
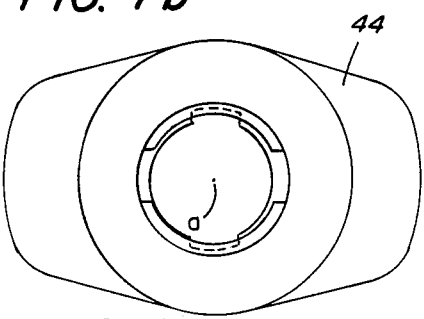

Referring next to FIGS. 8A and 8B another embodiment of the invention will be disclosed. In this instance the projections 54 are located on the flanges 40 and 42 and the slots 56 are formed in the cap extending outwardly from the opening 46. The procedure for assembling and locking is identical with that in the FIG. 7 embodiment. The slots and projections being aligned to assemble and rotated out of alignment to effect locking.

Figure 9A:
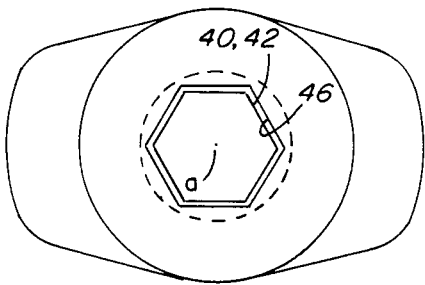
Figure 9B:
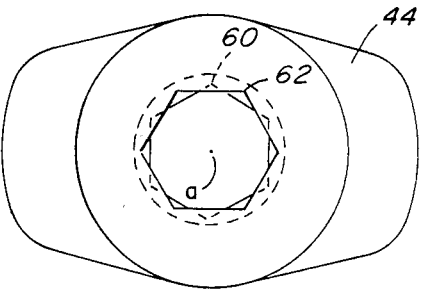

Referring next to FIGS. 9A and 9B another embodiment of the invention will be described. The opening 46 in the cap may be in the form of a polygon (in this instance, a hexagon). The flanges 40 and 42 on the plunger rod are also formed as hexagons of slightly smaller dimension. In assembly, the flange and the opening 46 are aligned as shown in FIG. 9A and being so aligned will pass through the opening. To lock the plunger in retracted position, the plunger rod 36 is rotated about its axis a so that the apexes 60 of the hexagonal flange locks behind the flats 62 of the walls of the opening 46 in the cap.

Figure 10A:
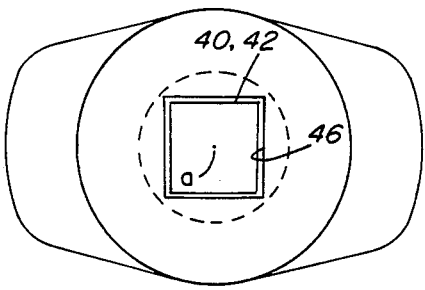
Figure 10B:
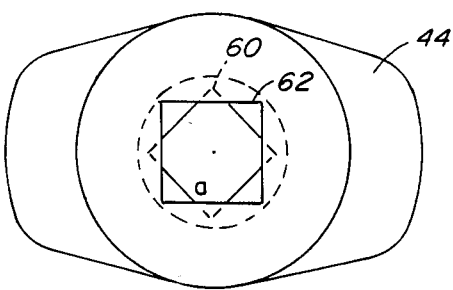

As seen in FIGS. 10A and 10B the flanges 40 and 42 are shown as squares of slightly smaller dimension than the opening 46 in the cap which is also a square. To lock the flange and cap together, as in the prior embodiments, the plunger rod is rotated until the apexes 60 of the flange are located behind the flat sides 62 of the square opening in the cap 46.

In each of these embodiments, either the flange 40 or 42 may interlock with the cap.

We claim:

1. A multipurpose syringe for obtaining a blood sample and for storing and shipping it comprising:
    a barrel having openings at its forward and rearward ends in communication with its interior, a plunger within the barrel slidable in sealing engagement with the inner wall of the barrel between forward and retracted positions, a plunger rod, one end of which mounts the plunger and the other end of which extends out of the rearward end of the barrel and,
    means to releasably lock the plunger in retracted position comprising:
    a pair of spaced flanges of discernible configuration extending outwardly from the axis of the rod and located adjacent the plunger,
    a cap removably secured to the rearward end of the barrel and having an opening which is larger than the flanges and of similar discernible configuration to permit passage of the flanges through the cap,
    mating interference means associated with the flanges and the opening in the cap and constructed to permit both flanges to pass through the opening in the cap when the interference means are angularly aligned with each other and to lock one flange to the cap when it has been withdrawn through the opening and the rod is rotated about its axis to position the interference means out of alignment with each other.

2. A multipurpose syringe for obtaining a blood sample and for storing and shipping it comprising:
    a barrel having openings at its forward and rearward ends in communication with its interior, a plunger within the barrel and slidable in sealing engagement with the inner wall of the barrel between forward and retracted positions, a plunger rod, one end of which mounts the plunger and the other end of which extends out of the rearward end of the barrel and
    means to releasably lock the plunger in retracted position comprising:
    a pair of spaced flanges of discernible configuration extending outwardly from the axis of the rod and located adjacent the plunger, a cap removably secured to the rearward end of the barrel and having an opening which is larger than the flanges and of similar discernible configuration to permit passage of the flanges through the cap, at least one slot in each flange extending inwardly toward the axis of the rod, at least one projection on the cap extending inwardly into the opening, which projection is smaller than the slots in the flanges to permit both flanges to pass through the opening in the cap when the slots are aligned with the projection and to lock one flange to the cap when it has been withdrawn through the opening and the rod is rotated about its axis to position the slot out of alignment with the projection.

3. A multipurpose syringe for obtaining a blood sample and for storing and shipping it comprising:

a barrel having openings at its forward and rearward ends in communication with its interior, a plunger within the barrel and slidable in sealing engagement with the inner wall of the barrel between forward and retracted positions, a plunger rod, one end of which mounts the plunger and the other end of which extends out of the rearward end of the barrel and means to releasably lock the plunger in retracted position comprising:

a pair of spaced flanges of discernible configuration extending outwardly from the axis of the rod and located adjacent the plunger, a cap removably secured to the rearward end of the barrel and having an opening which is larger than the flanges and of similar discernible configuration to permit passage of the flanges through the cap, at least one projection on each flange extending outwardly from the axis of the rod, at least one slot in the cap extending outwardly from the opening, which slot is larger than the projection on the flanges to permit both flanges to pass through the opening in the cap when the projections are aligned with the slot and to lock one flange to the cap when it has been withdrawn through the opening and the rod is rotated about its axis to position the projection out of alignment with the slot.

4. A syringe according the claim 1 wherein the configuration of the opening in the cap and the flanges on the rod are circles.

5. A syringe according to claim 1 wherein the configuration of the opening in the cap and the flanges on the rod are polygons having the same number of sides.

6. A syringe according to claim 1 wherein the configuration of the opening in the cap and the flanges on the rod are hexagons.

7. A syringe according the claim 1 wherein the configuration of the opening in the cap and the flanges on the rod are squares.

8. A syringe according to claim 1 wherein the rod is weakened for breaking adjacent the flange remote from the plunger.

9. A syringe according to claim 2 wherein the rod is weakened for breaking adjacent the flange remote from the plunger.

10. A syringe according to claim 3 wherein the rod is weakened for breaking adjacent the flange remote from the plunger.

11. A syringe according to claim 1 wherein a self sealing plug is located in the forward end of the barrel.

12. A syringe according to claim 2 wherein a self sealing plug is located in the forward end of the barrel.

13. A syringe according to claim 3 wherein a self sealing plug is located in the forward end of the barrel.

14. A syringe according the claim 1 wherein a self sealing plug is located in the forward end of the barrel and there are means on the forward end for mounting an inwardly projecting needle for piercing the plug.

15. A syringe according the claim 2 wherein a self sealing plug is located in the forward end of the barrel and there are means on the forward end for mounting an inwardly projecting needle for piercing the plug.

16. A syringe according the claim 3 wherein a self sealing plug is located in the forward end of the barrel and there are means on the forward end for mounting an inwardly projecting needle for piercing the plug.

17. A syringe according the claim 1 wherein a self sealing plug is located in the forward end of the barrel and there are means on the forward end for mounting an inwardly projecting needle for piercing the plug and for mounting a venipuncture needle.

18. A syringe according the claim 2 wherein a self sealing plug is located in the forward end of the barrel and means on the forward end for mounting an inwardly projecting needle for piercing the plug and for mounting a veinpuncture needle.

19. A syringe according the claim 3 wherein a self sealing plug is located in the forward end of the barrel and means on the forward end for mounting an inwardly projecting needle for piercing the plug and for mounting a venipuncture needle.

* * * * *